US00PP29206P3

(12) United States Plant Patent
van Sambeek

(10) Patent No.: US PP29,206 P3
(45) Date of Patent: Apr. 3, 2018

(54) *GAILLARDIA* PLANT NAMED 'BARGAISPINYEL'

(50) Latin Name: *Gaillardia×grandiflora*
Varietal Denomination: Bargaispinyel

(71) Applicant: Ellen van Sambeek, Aalsmeer (NL)

(72) Inventor: Ellen van Sambeek, Aalsmeer (NL)

(73) Assignee: Dümmen Group B.V., De Lier (NL)

( * ) Notice: Subject to any disclaimer, the term of this patent is extended or adjusted under 35 U.S.C. 154(b) by 35 days.

(21) Appl. No.: 15/330,237

(22) Filed: Aug. 27, 2016

(65) Prior Publication Data

US 2018/0064014 P1 Mar. 1, 2018

(51) Int. Cl.
*A01H 5/02* (2006.01)

(52) U.S. Cl.
USPC ..... Plt./431

(58) Field of Classification Search
USPC ..... Plt./431
See application file for complete search history.

*Primary Examiner* — Keith O Robinson
(74) *Attorney, Agent, or Firm* — C. A. Whealy

(57) ABSTRACT

A new and distinct cultivar of *Gaillardia* plant named 'Bargaispinyel', characterized by its compact and mounded plant habit; freely branching habit; strong leaves that resist yellowing; early and freely flowering habit; and large single inflorescences with greyed purple-colored ray florets with yellow-colored apices.

1 Drawing Sheet

Botanical designation: *Gaillardia×grandiflora.*
Cultivar denomination: 'BARGAISPINYEL'.

BACKGROUND OF THE INVENTION

The present invention relates to a new and distinct cultivar of *Gaillardia* plant, botanically known as *Gaillardia×grandiflora* and hereinafter referred to by the name 'Bargaispinyel'.

The new *Gaillardia* plant is a product of a planned breeding program conducted by the Inventor in Aalsmeer, The Netherlands. The objective of the breeding program is to create new compact *Gaillardia* plants with numerous attractive inflorescences and healthy leaves.

The new *Gaillardia* plant originated from a cross-pollination in July, 2013 of a proprietary selection of *Gaillardia×grandiflora* identified as code number GA-0011, not patented, as the female, or seed, parent with a proprietary selection of *Gaillardia×grandiflora* identified as code number GA-0099, not patented, as the male, or pollen, parent. The new *Gaillardia* plant was discovered and selected by the Inventor as a single flowering plant from within the progeny of the stated cross-pollination in a controlled environment in Aalsmeer, The Netherlands in February, 2014.

Asexual reproduction of the new *Gaillardia* plant by vegetative terminal cuttings in Aalsmeer, The Netherlands, since February, 2014 has shown that the unique features of this new *Gaillardia* plant are stable and reproduced true to type in successive generations.

SUMMARY OF THE INVENTION

Plants of the new *Gaillardia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Bargaispinyel'. These characteristics in combination distinguish 'Bargaispinyel' as a new and distinct *Gaillardia* plant:

1. Compact and mounded plant habit.
2. Freely branching habit.
3. Strong leaves that resist yellowing.
4. Early and freely flowering habit.
5. Large single inflorescences with greyed purple-colored ray florets with yellow-colored apices.

Plants of the new *Gaillardia* differ primarily from plants of the female parent selection in the following characteristics:

1. Plants of the new *Gaillardia* are more compact and stronger than plants of the female parent selection.
2. Plants of the new *Gaillardia* have stronger and healthier leaves than plants of the female parent selection.
3. Plants of the new *Gaillardia* flower earlier than plants of the female parent selection.

Plants of the new *Gaillardia* differ primarily from plants of the male parent selection in the following characteristics:

1. Plants of the new *Gaillardia* are more compact and stronger than plants of the male parent selection.
2. Plants of the new *Gaillardia* have stronger and healthier leaves than plants of the male parent selection.
3. Plants of the new *Gaillardia* flower earlier than plants of the male parent selection.
4. Plants of the new *Gaillardia* and the male parent selection differ in ray floret color as plants of the male parent selection have yellow-colored ray florets.

Plants of the new *Gaillardia* can be compared to plants of *Gaillardia×grandiflora* 'Sunset Cutie', disclosed in U.S. Plant Pat. No. 26,970. In side-by-side comparisons, plants of the new *Gaillardia* differ from plants of 'Sunset Cutie' in the following characteristics:

1. Plants of the new *Gaillardia* are more compact than plants of 'Sunset Cutie'.

2. Plants of the new *Gaillardia* are stronger than plants of 'Sunset Cutie'.
3. Plants of the new *Gaillardia* have smaller, stronger and healthier leaves than plants of 'Sunset Cutie'.
4. Inflorescences of plants of the new *Gaillardia* have fewer ray florets than inflorescences of plants of 'Sunset Cutie'.

BRIEF DESCRIPTION OF THE PHOTOGRAPH

The accompanying colored photograph illustrates the overall appearance of the new *Gaillardia* plant showing the colors as true as it is reasonably possible to obtain in colored reproductions of this type. Colors in the photograph may differ slightly from the color values cited in the detailed botanical description which accurately describe the colors of the new *Gaillardia* plant.

The photograph is a side perspective view of a typical flowering plant of 'Bargaispinyel' grown in a container.

DETAILED BOTANICAL DESCRIPTION

The aforementioned photograph and following observations and measurements describe plants grown in 13-cm containers during the summer in a glass-covered greenhouse in Aalsmeer, The Netherlands and under cultural practices typical of commercial *Gaillardia* production. During the production of the plants, day temperatures averaged 22° C. and night temperatures averaged 17° C. Plants were pinched one time and were three months old when the photograph was taken and six months old when the description was taken. In the following description, color references are made to The Royal Horticultural Society Colour Chart, 2007 Edition, except where general terms of ordinary dictionary significance are used.

Botanical classification: *Gaillardia×grandiflora* 'Bargaispinyel'.

Parentage:

*Female, or seed, parent*.—Proprietary selection of *Gaillardia×grandiflora* identified as code number GA-0011, not patented.

*Male, or pollen, parent*.—Proprietary selection of *Gaillardia×grandiflora* identified as code number GA-0099, not patented.

Propagation:

*Type*.—Terminal vegetative cuttings.

*Time to initiate roots, summer*.—About twelve days at temperatures about 26° C.

*Time to initiate roots, winter*.—About two weeks at temperatures about 23° C.

*Time to produce a rooted young plant, summer*.—About two weeks at temperatures about 23° C.

*Time to produce a rooted young plant, winter*.—About 16 days at temperatures about 18° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching, medium density.

Plant description:

*Plant and growth habit*.—Herbaceous perennial; compact and mounded plant habit; vigorous growth habit; freely branching habit with about 20 primary branches developing per plant.

*Plant height, soil level to top of foliar plane*.—About 21 cm.

*Plant height, soil level to top of floral plane*.—About 26 cm.

*Plant width*.—About 35 cm.

*Branch description*.—Length: About 25 cm. Diameter: About 6 mm. Internode length: About 3 cm. Strength: Strong. Aspect: Upright to about 30° from vertical. Texture and luster: Pubescent; matte. Color: Close to 147C.

*Leaf description*.—Arrangement: Alternate, simple; sessile. Length: About 11 cm. Width: About 2.5 cm. Shape: Oblanceolate; deeply lobed. Apex: Acute. Base: Attenuate. Margin: Entire. Texture and luster, upper and lower surfaces: Pubescent; matte. Venation pattern: Pinnate. Color: Developing leaves, upper surface: Close to 137C. Developing leaves, upper surface: Close to 137B. Fully developed leaves, upper surface: Close to 137B; venation, close to 138D. Fully developed leaves, lower surface: Close to 137C; venation, close to 146C.

Inflorescence description:

*Appearance*.—Single inflorescence form with recurving ray florets and tubular disc florets; inflorescences held mostly upright to outwardly on strong peduncles, inflorescences face mostly upright to outwardly; ray and disc florets develop acropetally on a capitulum.

*Fragrance*.—None detected.

*Flowering response*.—Plants begin flowering about eight weeks after planting; plants flower naturally during June and July in The Netherlands.

*Postproduction longevity*.—Inflorescences maintain good substance for about six weeks on the plant; inflorescences not persistent.

*Quantity of inflorescences*.—Freely flowering habit, about 70 inflorescences develop per plant during the flowering season.

*Inflorescence size*.—Diameter: About 14 cm. Depth (height): About 1.7 cm. Disc diameter: About 2.6 cm.

*Receptacles*.—Height: About 1.4 cm. Diameter: About 2.6 cm. Color: Close to 185A; center, close to 15A.

*Inflorescence buds*.—Height: About 8 mm. Diameter: About 1 cm. Shape: Flattened. Color: Close to 187B; mid-section, close to 144B.

*Ray florets*.—Quantity per inflorescence: About 16 arranged in a single whorl. Length: About 2.8 cm. Width: About 1.8 cm. Shape: Tri-lobed, moderately laciniate. Apex: Rounded, obtuse. Base: Attenuate. Margin: Entire. Aspect: Mostly upright. Texture and luster, upper surface: Smooth, glabrous; matte. Texture and luster, lower surface: Pubescent; lustrous. Color: When opening, upper and lower surfaces: Close to 179A; towards the apex, close to 13A. Fully opened, upper and lower surfaces: Close to 185A; towards the apex, close to 13A; color does not change with development.

*Disc florets*.—Quantity per inflorescence: About 144 massed at the center of the receptacle in about seven whorls. Length: About 1 cm. Diameter: About 1.5 mm. Shape: Fused tubular. Apex: Acute, five-pointed. Texture and luster, inner surface: Smooth, glabrous; lustrous. Texture and luster, outer surface: Pubescent; lustrous. Color: When opening, inner and outer surfaces: Close to 20A; towards the apex, lose to 187A. Fully opened, inner and outer surfaces: Close to 186B; towards the apex, close to 35A; color becomes closer to 186B with development.

*Involucral bracts*.—Quantity per inflorescence: About 42 arranged in about four whorls. Length: About 1.4 cm. Width: About 3 mm. Shape: Narrowly deltoid. Apex: Acute. Base: Fused, truncate. Margin: Entire, ciliate. Texture and luster, upper and lower surfaces: Slightly rough; matte. Color, upper and lower surfaces: Close to 144A.

*Peduncles*.—Length: About 11 cm. Diameter: About 3 mm. Strength: Strong. Aspect: Upright to about 30° from vertical. Texture and luster: Pubescent; semi-glossy. Color: Close to 146C.

*Reproductive organs*.—Androecium: Present on disc florets only. Quantity per floret: Five per disc floret. Filament length: About 4 mm. Filament color: Close to 155D. Anther length: About 3 mm. Anther shape: Oblong. Anther color: Close to 21A. Pollen amount: Moderate. Pollen color: Close to 162A. Gynoecium: Present on ray and disc florets. Quantity per floret: One. Pistil length: About 7 mm. Stigma shape: Two-lobed. Stigma diameter: Close to 1 mm. Stigma color: Close to 187A. Style length: About 7 mm. Style color: Close to 155B. Ovary color: Close to 149D.

*Seeds and fruits*.—Seed and fruit production have not been observed on plants of the new *Gaillardia*.

Disease & pest resistance: Plants of the new *Gaillardia* have not been observed to be resistant to pathogens and pests common to *Gaillardia* plants.

Garden performance: Plants of the new *Gaillardia* have been observed to have good garden performance and to tolerate wind and rain, to tolerate temperatures ranging from −15° C. to 35° C.

It is claimed:

1. A new and distinct *Gaillardia* plant named 'Bargaispin-yel' as illustrated and described.

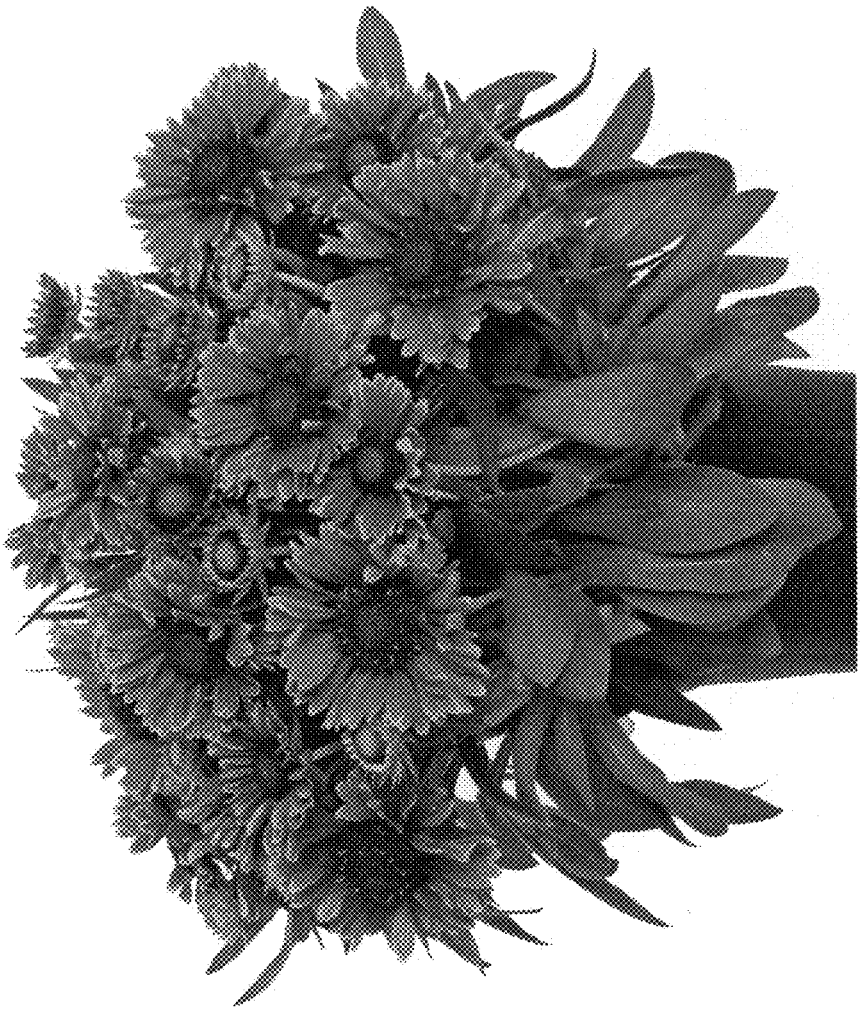

* * * * *